(12) United States Patent
Hartmann et al.

(10) Patent No.: US 8,233,963 B2
(45) Date of Patent: Jul. 31, 2012

(54) AUTOMATIC IDENTIFICATION OF TRACKED SURGICAL DEVICES USING AN ELECTROMAGNETIC LOCALIZATION SYSTEM

(75) Inventors: Steve Hartmann, Superior, CO (US); Jason Tipton, Westminster, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 1287 days.

(21) Appl. No.: 11/708,159

(22) Filed: Feb. 19, 2007

(65) Prior Publication Data

US 2008/0200927 A1    Aug. 21, 2008

(51) Int. Cl.
*A61B 5/05*    (2006.01)
(52) U.S. Cl. ...................................................... 600/424
(58) Field of Classification Search ................. 600/424
See application file for complete search history.

(56) References Cited

U.S. PATENT DOCUMENTS

| | | | |
|---|---|---|---|
| 4,705,038 A | 11/1987 | Sjostrom et al. | |
| 5,442,082 A | 8/1995 | Uphues et al. | |
| 5,610,811 A | 3/1997 | Honda et al. | |
| 5,740,808 A | 4/1998 | Panescu et al. | |
| 6,226,548 B1 | 5/2001 | Foley et al. | |
| 6,264,647 B1 | 7/2001 | Lechot et al. | |
| 6,381,485 B1 | 4/2002 | Hunter et al. | |
| 6,434,507 B1 * | 8/2002 | Clayton et al. | 702/152 |
| 6,540,739 B2 | 4/2003 | Lechot et al. | |
| 6,689,138 B2 | 2/2004 | Lechot et al. | |
| 6,861,954 B2 | 3/2005 | Levin | |
| 6,891,475 B2 | 5/2005 | Bui et al. | |
| 6,925,339 B2 | 8/2005 | Grimm et al. | |
| 7,567,834 B2 | 7/2009 | Clayton et al. | |
| 2002/0032380 A1 | 3/2002 | Acker et al. | |
| 2004/0215071 A1 | 10/2004 | Frank et al. | |
| 2004/0267297 A1 * | 12/2004 | Malackowski | 606/167 |
| 2005/0085714 A1 | 4/2005 | Foley et al. | |
| 2005/0085720 A1 | 4/2005 | Jascob et al. | |
| 2005/0215888 A1 | 9/2005 | Grimm et al. | |
| 2006/0029186 A1 | 2/2006 | De Villiers et al. | |
| 2006/0043179 A1 | 3/2006 | Nycz et al. | |
| 2006/0055712 A1 * | 3/2006 | Anderson | 345/647 |
| 2006/0094958 A1 | 5/2006 | Marquart et al. | |
| 2006/0142656 A1 | 6/2006 | Malackowski et al. | |
| 2006/0161059 A1 | 7/2006 | Wilson | |

(Continued)

FOREIGN PATENT DOCUMENTS

DE    10239710    3/2004

(Continued)

OTHER PUBLICATIONS

"Chips are just what the doctor ordered", article dated Nov. 14, 2006, The Sydney Morning Herald, http://www.smh.com.au/articles/2006/11/13/1163266481840.html?page=fullpage, printed Dec. 11, 2006 (2 pgs).

(Continued)

*Primary Examiner* — Brian Casler
*Assistant Examiner* — Saurel J Selkin
(74) *Attorney, Agent, or Firm* — Harness, Dickey

(57) ABSTRACT

A method and apparatus for identifying a member used in a navigation system. The navigation system can determine the identification of an instrument via an input. The input can be substantially automatic when an instrument is introduced into the navigation system field or assembly.

22 Claims, 5 Drawing Sheets

U.S. PATENT DOCUMENTS

| | | | |
|---|---|---|---|
| 2006/0173291 A1 | 8/2006 | Glossop | |
| 2006/0184396 A1 | 8/2006 | Dennis et al. | |
| 2006/0264742 A1 | 11/2006 | Neubauer et al. | |
| 2007/0016009 A1 | 1/2007 | Lakin et al. | |
| 2007/0249901 A1* | 10/2007 | Ohline et al. | 600/117 |
| 2008/0200926 A1 | 8/2008 | Verard et al. | |
| 2008/0200927 A1* | 8/2008 | Hartmann et al. | 606/130 |

FOREIGN PATENT DOCUMENTS

| | | |
|---|---|---|
| EP | 1518508 | 3/2005 |
| EP | 1719472 | 11/2006 |

OTHER PUBLICATIONS

"Maxim", DS2505 16-kbit Add-Only Memory, instruction manual, Dallas Semiconductor [undated] (24 pages).

Hoff, et al., Automatic Tool Identification and Registration, Colorado School of Mines, Feb. 26, 2005 (8 pages).

International Search Report and Written Opinion for PCT/US2008/001977 mailed Sep. 16, 2008 claiming benefit of U.S. Appl. No. 11/708,152, filed Feb. 19, 2007.

International Search Report and Written Opinion for PCT/US2008/001992 mailed Aug. 12, 2008 claiming benefit of U.S. Appl. No. 11/708,159, filed Feb. 19, 2007.

International Search Report and Written Opinion mailed Jun. 17, 2008 for PCT/US2008/001947.

Kiefer, Automatic Recognition of Medical Instruments, Using MATLAB to recognize medical tools with the use of fiducial markings, EGES510: Multidimensional Signal and Image Processing Final Project, Dec. 12, 2005 (19 pages).

L10-USB-Pen Reader, RFID 125 KHz, Part Nr 205 0014, data sheet, Version 1.02, MBBS S.A., 2005 (1 pg).

L10-USB-TRAY Reader, RFID 125 KHz, Part Nr 200 0016, data sheet, Version 1.02, MBBS S.A., 2005 (1 pg).

MediTAG™ metal 8.0, RFID 125 KHz, 2K Read/Write, Part Nr 103 0003, data sheet, Version 1.02, MBBS S.A., 2005 (1 pg).

MediTAG™ plastic 5.6, RFID 125 KHz, 2K Read/Write, Part Nr 105 0051, datasheet, Version 1.03, MBBS S.A., 2005 (1 pg).

MediTAG™ tray 70x40, RFID 125 KHz, 2K Read/Write, Part Nr 105 0059, data sheet, Version 1.03, MBBS S.A., 2005 (1 pg).

RFID, Information at the Surgeon's Fingertips, brochure, Precimed SA and MBBS SA, 2005 (6 pgs).

* cited by examiner

AUTOMATIC IDENTIFICATION OF TRACKED SURGICAL DEVICES USING AN ELECTROMAGNETIC LOCALIZATION SYSTEM

CROSS REFERENCE TO RELATED APPLICATIONS

This application is filed concurrently with U.S. patent application Ser. No. 11/708,157; filed on Feb. 19, 2007 entitled, "AUTOMATIC IDENTIFICATION OF INSTRUMENTS USED WITH A SURGICAL NAVIGATION SYSTEM"; and U.S. patent application Ser. No. 11/708,152; filed on Feb. 19, 2007 entitled, "MULTI-CONFIGURATION TRACKING ARRAY AND RELATED METHOD." The disclosures of the above applications are incorporated herein by reference.

FIELD

The present teachings relate generally to a surgical navigation system, and particularly to a system that allows for identification of a particular instrument during a navigated procedure.

BACKGROUND

Generally an anatomy, such as a human anatomy, allows for substantially natural operation thereof. However, various diseases, injuries, and the like can occur that can affect the natural operation of the anatomy. Surgical procedures can be performed to assist in repairing the anatomy.

Often access must be obtained to various portions of the anatomy to perform a selected procedure. The access portals can be large and multiple depending upon a particular procedure, issue in the anatomy, or the like. It is desirable, however, to provide a procedure that is the least invasive as possible to minimize recovery time, minimize collateral injury to the anatomy, or other appropriate reasons. For example, it is desirable to provide instruments that can be navigated within an anatomy while not being directly viewable by a surgeon.

Further, it is desirable to provide the multiple instruments for use during a single procedure. Each of these instruments can be different in size, shape, geometry, and the like. Therefore, it is desirable to provide a system that can know or identify a particular instrument without additional intervention of a surgeon, user, or any appropriate individual.

SUMMARY

A method and apparatus are taught herein that allows for identification of the various surgical instruments during a surgical procedure. In particular, when using an electromagnetic tracking system in a navigation system, a distortion in a field can be used to identify a particular instrument. Therefore, a predetermined and selected distortion or distortion pattern can be provided to identify particular instruments. The navigation system can then use the identification of the instrument when providing a navigation or display of the instrument for use by a surgeon.

According to various embodiments, a navigation system to navigate a procedure on an anatomy is disclosed. The system can include an instrument operable to be moved relative to the anatomy. An identification member can be associated with the instrument and an identification member reader can be provided to determine information from the identification member. A processor can identify the instrument based at least in part on the information obtained by the identification member reader from the identification member. Also, a tracking device can be associated with the instrument that can be tracked with a tracking system.

According to various embodiments, a navigation system to be used with navigating a surgical procedure on an anatomy is disclosed. The system can include an instrument to be used to perform an intervention on the anatomy and an instrument identification portion and tracking device associated with the surgical instrument. A tracking system can determine a position of the tracking device relative to a reference point. A processor can determine a position of a working portion of the instrument based in part at least on the tracking system and the instrument identification portion.

According to various embodiments, a method of navigating a surgical procedure relative to an anatomy is disclosed. The method can include selecting a surgical instrument with an working portion and providing an identification portion with the instrument. A processor can determine the identity of the instrument with the identification portion. A position of the working portion relative to a reference point can be determined, based at least in part on the determined identity of the instrument. The instrument can be navigated relative to the anatomy.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses.

Figure 1:
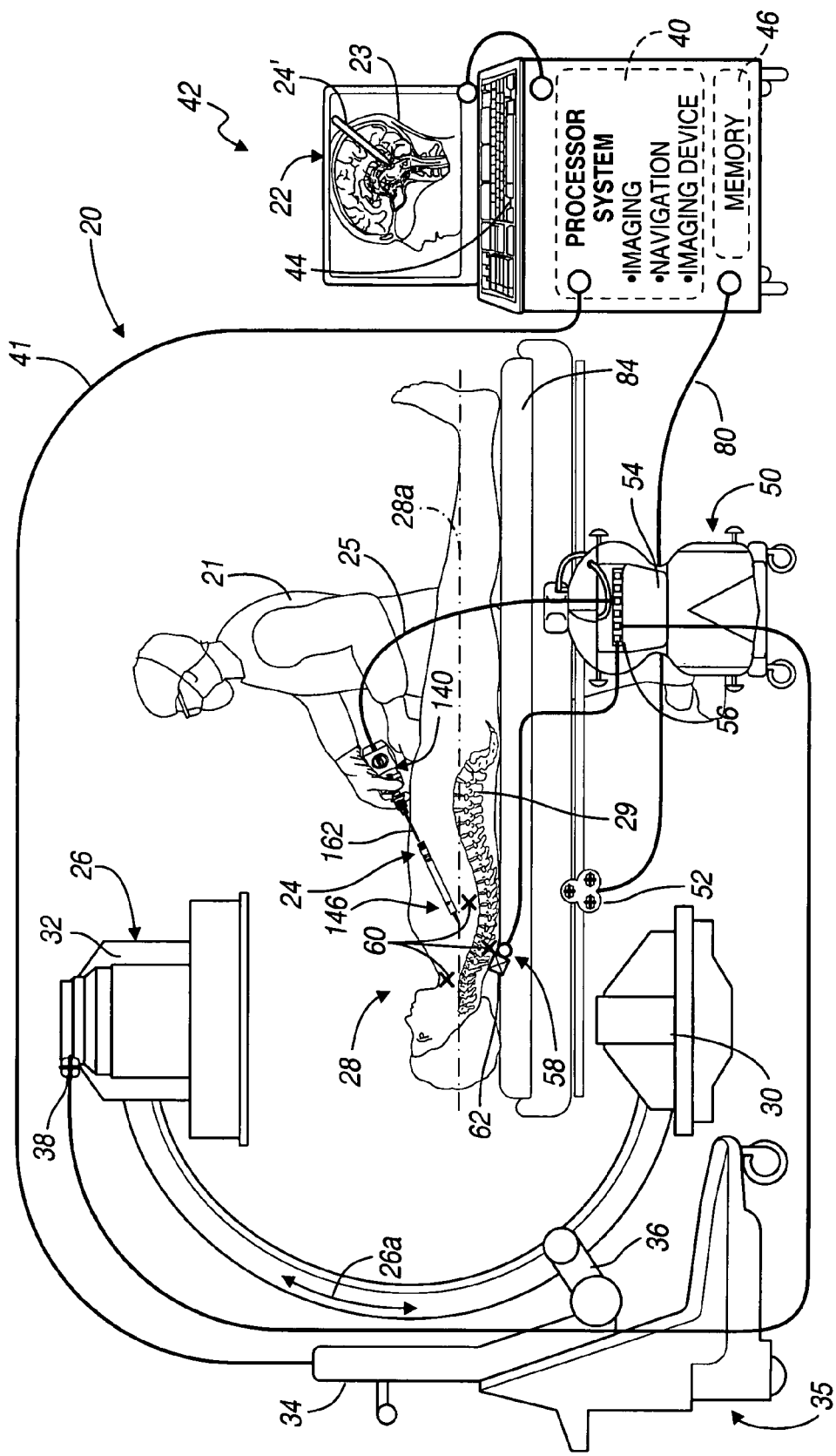
FIG. 1 is an environmental view of a surgical navigation system according to various embodiments.

A guided procedure can be performed with a navigation system 20, illustrated in FIG. 1. The guided procedure can be any appropriate procedure, such as a neural procedure, spinal procedure, and orthopedic procedure. The navigation system 20 can include various components, as will be discussed further herein. The navigation system 20 can allow a user, such as a surgeon 21, to view on a display device 22 a relative position of an instrument 24 to a coordinate system. The coordinate system can be made relative to image data displayed on the display 22, such as in an image guided procedure, or can be registered to a patient only, such as in an imageless procedure. Although it can also be registered to atlas data, a reference point outside the patient, or any other appropriate location.

It should further be noted that the navigation system 20 can be used to navigate or track various instruments including: catheters, probes, needles, guidewires, instruments, implants, deep brain stimulators, electrical leads, etc. Moreover, the instrument 24 can be used in any region of the body. The navigation system 20 and the various instruments 24 can be used in any appropriate procedure, such as one that is generally minimally invasive, arthroscopic, percutaneous, stereotactic, or an open procedure. Also, the illustrated instrument 24 is only exemplary of any appropriate instrument and may also represent many instruments, such as a series or group of instruments. Identity and other information relating to the instrument 24 can also be provided to the navigation system 20, as discussed further herein. The information about the instrument 24 can also be displayed on the display 22 for viewing by the surgeon 21.

The navigation system 20 can include an imaging device 26 that is used to acquire pre-, intra-, or post-operative or real-time image data of a patient 28. The imaging device 26 can be, for example, a fluoroscopic x-ray imaging device that may be configured as, and also referred to as, a C-arm 26 having an x-ray source 30 and an x-ray receiving or intensifier section 32. An optional calibration and tracking target and optional radiation sensors can be provided, as understood by one skilled in the art. An example of a fluoroscopic C-arm x-ray device that may be used as the imaging device 26 is the ARCADIS® Orbic or ARCADIS® Orbic 3D from Siemens Medical of Germany. Other exemplary fluoroscopes include bi-plane fluoroscopic systems, ceiling fluoroscopic systems, cath-lab fluoroscopic systems, fixed C-arm fluoroscopic systems, 3D fluoroscopic systems, O-arm™ imaging devices (i.e. devices sold by Breakaway Imaging, LLC. having a place of business in Massachusetts, USA), etc.

An optional imaging device controller 34 can control the imaging device 26 to capture the x-ray images received at the receiving section 32 and store the images for later use. The controller 34 may also be separate from the C-arm 26 or located a distance from the C-arm 26. The controller 34 can control the C-arm 26 to control movement in the direction of arrow 26a or rotate about a longitudinal axis 28a of a patient 28, allowing anterior or lateral views of the patient 28 to be imaged. Each of these movements involves rotation about a mechanical axis 36 of the C-arm 26.

The operation of the C-arm 26 is understood by one skilled in the art. Briefly, x-rays can be emitted from an x-ray section 30 and received at a receiving section 32. The receiving section 32 can include a camera that can create the image data from the received x-rays. Further, a C-arm tracking device 38 can be provided to track a position of any portion of the C-arm 26, such as the receiving section 32, at any appropriate time by the navigation system 20.

The image data can be forwarded from the C-arm controller 34 to a navigation computer and/or processor system 40 via a communication system 41. The processor system 40 can also include the C-arm controller 34. The processor system 40 can process the image data, navigation data, etc. The processor system 40 can include one or more separate processors. The communication system 41 can be wireless, wired, a data transfer device (e.g. a CD-Rom or DVD-Rom), or any appropriate system. A work station 42 can include the processor system 40, the display 22, a user interface 44, and a memory 46. It will also be understood that the image data is not necessarily first retained in the controller 34, but may be directly transmitted to the workstation 42 or to a tracking system 50, as discussed herein.

The work station 42 provides facilities for displaying the image data as an image on the display 22, saving, digitally manipulating, or printing a hard copy image of the received image data. The user interface 44 may be a keyboard, mouse, touch pen, touch screen or other suitable device. The user interface 44 allows a user to provide inputs to control the imaging device 26, via the C-arm controller 34, or adjust the display settings of the display 22.

While the imaging device 26 is shown in FIG. 1, any other alternative 2D, 3D or 4D imaging modality may also be used. As disclosed herein any appropriate imaging system can be used in the navigation system to provide image data. The imaging system can generally provide information regarding movement of a capturing portion thereof to determine a position of the capturing portion relative to the patient 28. For example, any 2D, 3D or 4D imaging device, such as isocentric fluoroscopy, bi-plane fluoroscopy, ultrasound, computed tomography (CT), multi-slice computed tomography (MSCT), T1 weighted magnetic resonance imaging (MRI), T2 weighted MRI, high frequency ultrasound (HIFU), positron emission tomography (PET), optical coherence tomography (OCT), intra-vascular ultrasound (IVUS), ultrasound, intra-operative CT, single photo emission computed tomography (SPECT), or planar gamma scintigraphy (PGS) may also be used to acquire 2D, 3D or 4D pre- or post-operative and/or real-time images or image data of the patient 28. The images may also be obtained and displayed in two, three or four dimensions. In more advanced forms, four-dimensional surface rendering regions of the body may also be achieved by incorporating patient data or other data from an atlas or anatomical model map or from pre-operative image data captured by MRI, CT, or echocardiography modalities. A more detailed discussion on optical coherence tomography (OCT), is set forth in U.S. Pat. No. 5,740,808, issued Apr. 21, 1998, entitled "Systems And Methods For Guiding Diagnostic Or Therapeutic Devices In Interior Tissue Regions" which is hereby incorporated by reference.

It will be understood that image data can be created or captured with any appropriate imaging device, such as a magnetic resonance imaging system, a positron emission tomography system, computed tomography, or any appropriate system. Also, intraoperative MRI systems can be used to create image data of the patient 28 during an operative procedure. Intraoperative MRI systems can include the Pole Star™ N20 distributed by Medtronic, Inc. It will be further understood that various imaging systems can be calibrated according to various known techniques.

Image datasets from hybrid modalities, such as positron emission tomography (PET) combined with CT, or single photon emission computer tomography (SPECT) combined with CT, can also provide functional image data superimposed onto anatomical data to be used to confidently reach target sites within the patient 28. It should further be noted that the optional imaging device 26, as shown in FIG. 1, provides a virtual bi-plane image using a single-head C-arm fluoroscope as the optional imaging device 26 by simply rotating the C-arm 26 about at least two planes, which could be orthogonal planes to generate two-dimensional images that can be converted to three-dimensional volumetric images. By acquiring images in more than one plane, an icon representing the location of an impacter, stylet, reamer driver, taps, drill, deep brain stimulators, electrical leads, needles, implants, probes, or other instrument, introduced and advanced in the patient 28, may be superimposed in more than one view on the display 22 allowing simulated bi-plane or even multi-plane views, including two and three-dimensional views.

With continuing reference to FIG. 1, the navigation system 20 can further include the tracking system 50 that includes a localizer 52 (e.g. a coil array or multiple coil arrays when an electromagnetic (EM) tracking system is provided), a coil array controller 54, and a navigation probe or device interface (NPI) 56. The tracking system can also include various trackable members or devices such as the imaging device tracking device 38, a dynamic reference frame 58, or an instrument tracking device 94. Each of these can interconnect with the NPI 56. The dynamic reference frame 58 can include a dynamic reference frame member or holder 60 and the removable tracking device 62. Alternatively, the dynamic reference frame 58 can include a tracking device that is formed integrally with the dynamic reference frame member 60. One skilled in the art will understand that the tracking device 62 can be any appropriate device that can be an emitter, a receiver, a reflector, a sensor to sense a field, or any other appropriate device that can be tracked by a tracking system including the localizer 52.

The localizer coil array 52 may also be supplemented or replaced with a second localizer 52*a*. The second localizer 52*a* may be the same as the first localizer 52 or different, such as that described in U.S. patent application Ser. No. 10/941,782, filed Sep. 15, 2004, now U.S. Pat. App. Pub. No. 2005/0085720, and entitled "METHOD AND APPARATUS FOR SURGICAL NAVIGATION", herein incorporated by reference. As is understood, the localizer array can transmit signals that are received by the tracking device 62 of the dynamic reference frame 58, the instrument tracking device 94, the imaging device tracking device 38, or any other tracking device. The dynamic reference frame 58, the instrument tracking device 94, the imaging tracking device 38, can then transmit signals based upon the received signals from the array 52, 52*a*. One skilled in the art will also understand that the localizer 52, 52*a* can receive or sense an EM field produced by the various tracking devices 62, 94, 38 as well. Thus the system can work in either manner or a combination.

It should further be noted that the entire tracking system 50 or parts of the tracking system 50 may be incorporated into the imaging device 26. For example, one of the localizers can be incorporated into the imaging device 26. Incorporating the tracking system 50 may provide an integrated imaging and tracking system. Any combination of these components may also be incorporated into the imaging system 26, which can include any appropriate imaging device. For example, the coil array 52 can be positioned in the receiving section 32. The coil array 52 can be an electromagnetic array for use in an electromagnetic tracking system.

While, the localizer or coil array 52 can be attached to the receiving section 32 of the C-arm 26, it should be noted, however, that the coil array 52 may also be positioned at any other location as well. For example, the coil array 52 may be positioned at the x-ray source 30, within or atop an operating room (OR) table 84, positioned below the patient 28, on siderails associated with the OR table 84, or positioned on the patient 28 in proximity to the region being navigated, such as on the patient's chest. The coil array 52 may also be positioned in the items being navigated, further discussed herein.

The coil array 52 can include a plurality of coils each operable to generate distinct electromagnetic fields into the navigation region of the patient 28, which is sometimes referred to as patient space. Electromagnetic systems are generally described in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The coil array 52 is controlled or driven by the coil array controller 54. The coil array controller 54 can drive each coil in the coil array 52 in a time division multiplex or a frequency division multiplex manner. In this regard, each coil may be driven separately at a distinct time or all of the coils may be driven simultaneously with each being driven by a different frequency, as discussed further herein. This arrangement makes the coil array 52, a transmitter coil array. It will be understood that the coil array may also receive, as discussed above. Thus, reference to a transmitter coil array is merely exemplary and not intended to limit the type of localizer used in a selected tracking system.

Upon driving the coils in the transmitter coil array 52 with the coil array controller 54, electromagnetic fields are generated within the patient 28 in the area where the medical procedure is being performed, which is again sometimes referred to as patient space. The electromagnetic fields generated in the patient space induce currents in the tracking devices 38, 62, 94 positioned in the navigation field. These induced signals are delivered to the navigation device interface 56 and can be forwarded to the coil array controller 54. Again, it will be understood that the tracking devices may transmit a field and induce a signal in the localizer 52.

The navigation device interface 54 may provide all the necessary electrical isolation for the navigation system 20, as discussed herein. The navigation device interface 56 can also include amplifiers, filters and buffers to directly interface with the tracking devices 38, 62, 94. Alternatively, the tracking devices 38, 62, 94, or any other appropriate portion, may employ a wireless communications channel, such as that disclosed in U.S. Pat. No. 6,474,341, entitled "Surgical Communication Power System," issued Nov. 5, 2002, herein incorporated by reference, as opposed to being coupled with a physical transmission line to the navigation device interface 56.

When the navigation system 20 uses an EM based tracking system, various portions of the navigation system 20, such as tracking devices 62, 94, that can be associated with the (DRF) 58 and the instrument 24, are equipped with at least one, and generally multiple coils, which are operable with the EM localizer arrays 52, 52*a*. Alternatively, the tracking system 50 may be a hybrid system that includes components from various tracking systems such as optical, acoustic, radiation, radar, etc.

The tracking device 94 associated with the instrument 24 can be in a handle or inserter that interconnects with an attachment. The instrument may be or may assist in placing an implant or in driving a selected portion. The instrument 24 can include a graspable or manipulable portion 140 (FIG. 3) at a proximal end and the tracking device 94 can be fixed near the manipulable portion of the instrument 24 or at a distal working end. The tracking device 94 can include an electromagnetic sensor to sense the electromagnetic field generated by the transmitter coil array 52 that can induce a current in the tracking device 94, or vice versa as discussed above. The tracking device 94 can also be used to identify the instrument 24, as discussed herein. Alternatively, the tracking device element 94 may be used only to identify the instrument 24, while a second system tracks the instrument 24 to determine its position.

The dynamic reference frame 58 of the tracking system 50 can also be coupled to the navigation device interface 56 to forward the information to the coil array controller 54. The dynamic reference frame 58, according to various embodiments, may include a small magnetic field detector as the tracking device 62. The dynamic reference frame 58 may be fixed to the patient 28 adjacent to the region being navigated so that any movement of the patient 28 is detected as relative motion between the transmitter coil array 52 and the dynamic reference frame 58. The dynamic reference frame 58 can be interconnected with the patient 28 in any appropriate manner, including those discussed herein. Any relative motion is forwarded to the coil array controller 54, which updates registration correlation and maintains accurate navigation, further discussed herein. An electromagnetic dynamic reference frame 58 can be configured as a pair or trio of orthogonally oriented coils, each having the same center or may be configured in any other non-coaxial or co-axial coil configuration.

The dynamic reference frame 58 may be affixed externally to the patient 28, adjacent to the region of navigation, such as on the patient's cranium, etc., as shown in FIG. 1. The dynamic reference frame 58 can be affixed to the patient's skin, by way of a selected adhesive patch and/or a tensioning system. The dynamic reference frame 58 may also be removably attachable to a fiducial marker 69. The fiducial markers can be anatomical landmarks or members attached or positioned on the patient's 28 body. The dynamic reference frame 58 can also be connected to a bone portion of the anatomy. The bone portion can be adjacent the area of the procedure, the bone of the procedure, or any appropriate body portion.

Although the discussion above is directed to an electromagnetic navigation and tracking system, it will be understood that any appropriate tracking system can be used as the tracking system 50. For example, one skilled in the art will understand that appropriate tracking systems include, but are not limited to, an optical tracking system, a radar tracking system, an acoustic tracking system, an accelerometer tracking system. Nevertheless, the tracking system can include any appropriate portions such as an appropriate localizer for the tracking system and appropriate tracking devices for the tracking system. Thus, the discussion herein regarding an electromagnetic tracking system is merely exemplary of any appropriate tracking system. Also, more than one tracking system can be used during a procedure, such as a hybrid system discussed above. Thus, an EM and an optical tracking system can be used at the same time to track within the same space.

Briefly, the navigation system 20 operates as follows. The navigation system 20 creates a translation map between all points in the image data or image space and the corresponding points in the patient's anatomy in patient space. After this map is established, the image space and patient space are registered. In other words, registration is the process of determining how to correlate a position in image space with a corresponding point in real or patient space. This can also be used to illustrate a position of the instrument 24 relative to the proposed trajectory and/or the determined anatomical target. The work station 42 in combination with the coil array controller 54 and the C-arm controller 34 identify the corresponding point on the pre-acquired image or atlas model relative to the tracked instrument 24 and display the position on display 22 and relative to the image data 23. This identification is known as navigation or localization. An icon representing the localized point or instruments is shown on the display 22 within several two-dimensional image planes, as well as on three and four dimensional images and models.

To register the patient 28, the surgeon 21 may use point registration by selecting and storing particular points from the pre-acquired images and then touching the corresponding points on the patient's 28 anatomy with a pointer probe or any appropriate tracked device, such as the instrument 24. The navigation system 20 analyzes the relationship between the two sets of points that are selected and computes a match, which allows for a determination of a correlation of every point in the image data or image space with its corresponding point on the patient's anatomy or the patient space.

The points that are selected to perform registration or form a translation map are the fiducial markers 69, such as anatomical or artificial landmarks. Again, the fiducial markers 69 are identifiable on the images and identifiable and accessible on the patient 28. The fiducial markers 69 can be artificial landmarks that are positioned on the patient 28 or anatomical landmarks that can be easily identified in the image data. The artificial fiducial markers 69, can also form part of the dynamic reference frame 58, such as those disclosed in U.S. Pat. No. 6,381,485, entitled "Registration of Human Anatomy Integrated for Electromagnetic Localization," issued Apr. 30, 2002, herein incorporated by reference. It will be understood that the "X" illustrated in FIG. 1 can merely indicate a position of a fiducial marker 69 rather than being the fiducial marker 69.

The navigation system 20 may also perform registration using anatomic surface information or path information as is known in the art (and may be referred to as auto-registration). The system 20 may also perform 2D to 3D registration by utilizing the acquired 2D images to register 3D volume images by use of contour algorithms, point algorithms or density comparison algorithms, as is known in the art. An exemplary 2D to 3D registration procedure is set forth in U.S. Ser. No. 10/644,680, filed on Aug. 20, 2003, now U.S. Pat. App. Pub. No. 2004-0215071, entitled "Method and Apparatus for Performing 2D to 3D Registration", incorporated herein by reference.

In order to maintain registration accuracy, the navigation system 20 can continuously track the position of the patient 28 during registration and navigation with the dynamic reference frame 58. This is because the patient 28, dynamic reference frame 58, and transmitter coil array 52 may all move during the procedure, even when this movement is not desired. Alternatively the patient 28 may be held immobile once the registration has occurred, such as with a head frame. Therefore, if the navigation system 20 did not track the position of the patient 28 or area of the anatomy, any patient movement after image acquisition would result in inaccurate navigation within that image. The dynamic reference frame 58 allows the tracking system 50 to track the anatomy and can assist in registration. Because the dynamic reference frame 58 is rigidly fixed to the patient 28, any movement of the anatomy or the transmitter coil array 52 is detected as the relative motion between the transmitter coil array 52 and the dynamic reference frame 58. This relative motion is communicated to the coil array controller 54, via the navigation probe interface 56, which updates the registration correlation to thereby maintain accurate navigation.

The dynamic reference frame 58 can be affixed to any appropriate portion of the patient 28, and can be used to register the patient space to the image data, as discussed above. For example, when a procedure is being performed relative to a spine 29, the dynamic reference frame 58 can be interconnected with or near the spine 29. The dynamic reference frame 58 can be interconnected with the spine 29 in any appropriate manner, such as those discussed herein according to various embodiments.

The navigation system 20 can detect both the position of the patient's anatomy and the position of the tracking device 94 attached to the instrument 24. Knowing the location of these two items allows the navigation system 20 to compute and display the position of the instrument 24 or any portion thereof in relation to the patient 28, after registration. The tracking system 50 is employed to track the instrument 24 and the anatomy 28 simultaneously.

The tracking system 50, if it is using an electromagnetic tracking assembly, can work by positioning the transmitter coil array 52 adjacent to the patient space to generate an EM field, which can be low energy, generally referred to as a navigation field. Because every point in the navigation field or patient space is associated with an unique field strength, the electromagnetic tracking system 50 can determine the position of the instrument 24 by measuring the field strength at the tracking device 94 location. The dynamic reference frame 58 is fixed to the patient 28 to identify the location of the patient 28 in the navigation field. The electromagnetic tracking system 50 continuously recomputes the relative position of the dynamic reference frame 58 and the instrument 24 during localization and relates this spatial information to patient registration data to enable image guidance of the instrument 24 within and/or relative to the patient 28.

To obtain maximum accuracy, it can be selected to fix the dynamic reference frame 58 in each of at least 6 degrees of freedom. Thus, the dynamic reference frame 58 or any of the tracking sensors 38, 62, 94 can be fixed relative to axial motion X, translational motion Y, rotational motion Z, yaw, pitch, and roll relative to the portion of the patient 28 to which it is attached. Any appropriate coordinate system can be used to describe the various degrees of freedom. Fixing the dynamic reference frame 58 relative to the patient 28 in this manner can assist in maintaining maximum accuracy of the navigation system 20.

The instrument 24 can be any appropriate instrument (e.g., a catheter, a probe, a guide, etc.) and can be used for various procedures and methods, such as delivering a material to a selected portion of the patient 28, such as within the spine 29. Other exemplary instruments can also be implantable members, scissors, clamps, retractors, etc. The material can be any appropriate material such as a bioactive material, a pharmacological material, a contrast agent, or any appropriate material. As discussed further herein, the instrument 24 can be precisely positioned via the navigation system 20 and otherwise used to achieve a protocol for positioning the material relative to the patient 28. For example, the instrument 24 can be used to position and fix an implantable member relative to the spine 29.

Figure 2A:
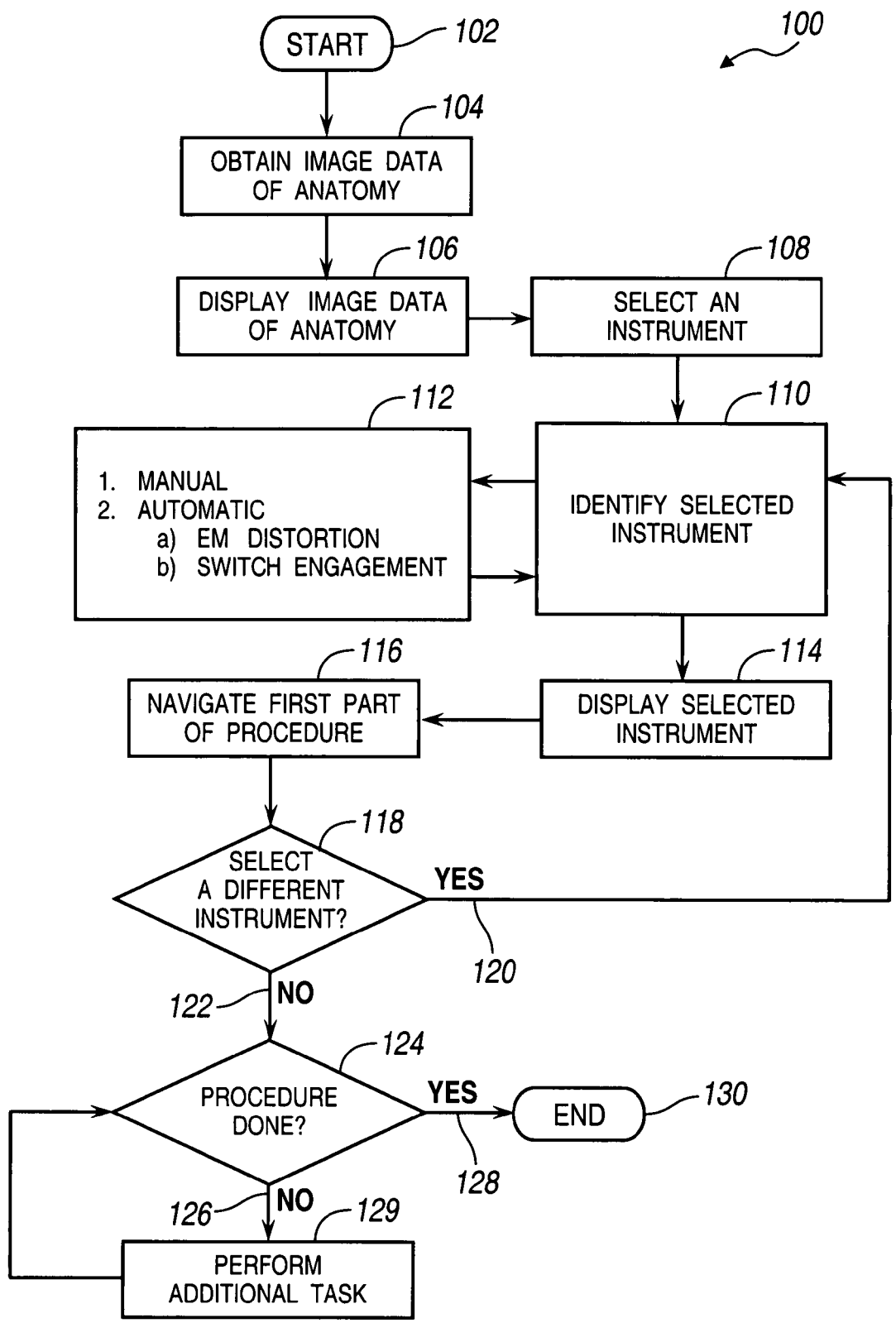
FIG. 2A is a flowchart illustrating an instrument identification system according to various embodiments.

With reference to FIG. 2A an identification system or method 100 is illustrated that can be used to identify an instrument, such as the instrument 24, for display on the display 22. It will be understood that the instrument 24 can be one or a plurality of instruments that can change during a procedure. Therefore, the particular instrument 24 that is displayed on the display 22 as the icon 24' can change from moment to moment. The identification system 100 can be provided to allow for identification of the instrument for display on the display 22 at the appropriate time.

The identification method 100 can begin at start block 102. The method 100 can include, as understood by one skilled in the art, obtaining image data of the anatomy in block 104. Additionally, the image data can be displayed in block 106. It will be understood that the obtaining of image data in block 104 and displaying of image data in block 106 is merely exemplary, and not required for the identification method 100. Nevertheless, for clarity of the current discussion, obtaining of image data in block 104 and displaying of image data in block 106 can be provided for a particular procedure.

The image data can be acquired with the imaging device 26, or any appropriate device. Also, the image data can be acquired intra-operatively or pre-operatively. Even in an instance when no image data is acquired or displayed of the patient 28, certain information can be displayed on the display 22. For example, atlas data, augmented atlas data, plane or line data, and the like can be displayed. For example, an atlas model can be displayed. The atlas model can be modified based upon specific information from the patient 28 or not.

An instrument can be selected in block 108. The instrument can be selected at any appropriate time. The instrument can be any appropriate instrument and can include a stylet, catheter, implant, or any appropriate portion. The selected instrument, however, can be the first instrument or any appropriate instrument in a series for use during a selected procedure. Again, the discussion of a selected instrument is simply provided for clarity of the current discussion and not intended to limit the breadth of the current teachings.

Once the instrument is selected in block 108, the selected instrument can be identified in block 110. The identification of the instrument can be performed in any appropriate manner, such as in the various steps illustrated in block 112. The identification of the instrument steps in block 112 can include manual identification or automatic identification. Manual identification can include selection from a menu, entering data into the work station 42, or any appropriate type of manual identification.

Automatic identification can include EM distortion identification, as discussed further herein. Automatic identification can also include a switch engagement or activation, also discussed further herein. The automatic identification, illustrated at block 112 can be substantially automatic or without intervention of the surgeon 21 or any other user. The automatic identification can allow for identification by the navigation system 20, the tracking system 50, the work station 42, or any appropriate portion of the instrument that is currently being used or engaged with the navigation system 20 without intervention by a user. This can allow for ease of use of the navigation system 20, an efficient reduction in the number of steps required to use the navigation system 20 or minimization of possible human error or minimization of error checking steps.

Once the instrument has been identified in block 110 an icon of the selected instrument can be displayed in block 114. The display of the instrument can be any appropriate display, such as the icon 24' superimposed on the image data 23 on the display 22. It will be understood that the icon 24' can substantially illustrate the selected instrument relative to the image data 23. An identification of the instrument in block 110 can assist in providing a substantially realistic and appropriate identification or display of the instrument on the display 22. For example, an instrument of a selected or unique geometry, size, configuration or the like can be displayed in an appropriate manner on the display 22.

With the instrument displayed on the display 22 from block 114, the procedure can be navigated or a first part of the procedure can be navigated, in block 116. It will be understood that the procedure can be navigated in block 116 without image data of the patient or without displaying the selected instrument on the display. For example, a substantially imageless system can be provided and the identification of the instrument in block 110 can be used to provide for an appropriate display of just the instrument relative to the reference frame, such as patient space, rather than in the image data 23. Therefore, obtaining or displaying image data is merely exemplary and not required.

Additionally, displaying the selected instrument, with the icon 24', on the display 22 is also not necessary. For example, the identification of the instrument in block 110 can be used simply to identify an instrument for use in the navigation system 20. The navigation system 20 can provide other types of feedback, rather than visual feedback, to the surgeon 21 or any other appropriate user, without requiring a display of the instrument. Therefore, it will be understood that the navigation of the first part of the procedure in block 116 can be with or without any type of visual display.

Once the selected instrument is used and a first portion of a procedure is navigated in block 116 a decision can be made as to whether a further instrument is to be identified in block 118. For example, the first portion of the navigated procedure may be to guide or use a tap. A driver may then be needed to drive an instrument into the tapped portion. Thus, the decision in block 118 may be to follow a YES path 120. If the YES path 120 is followed, then the procedure will proceed back to block 108 to selected an instrument. From block 108 the instrument can be identified in a manner substantially similar to the initial instrument.

If the determination is NO 122 then a second decision block can be reached. The second decision block is for determining whether the procedure is done in block 124. If the decision is NO, then path 126 can be followed to perform additional tasks in block 129. If the procedure is done, then the YES path 128 can be followed to end the procedure in block 130. Thus, a procedure can be performed with the identification of the appropriate instruments for navigation of a procedure, relative to the patient 28, or any appropriate anatomy. The identification of the instrument can be substantially automatic so that a user, such as the surgeon 21 is not required to perform any steps to insure that the navigation system 20 or any portion thereof, understands or includes data of the particular instrument being used.

Figure 2B:
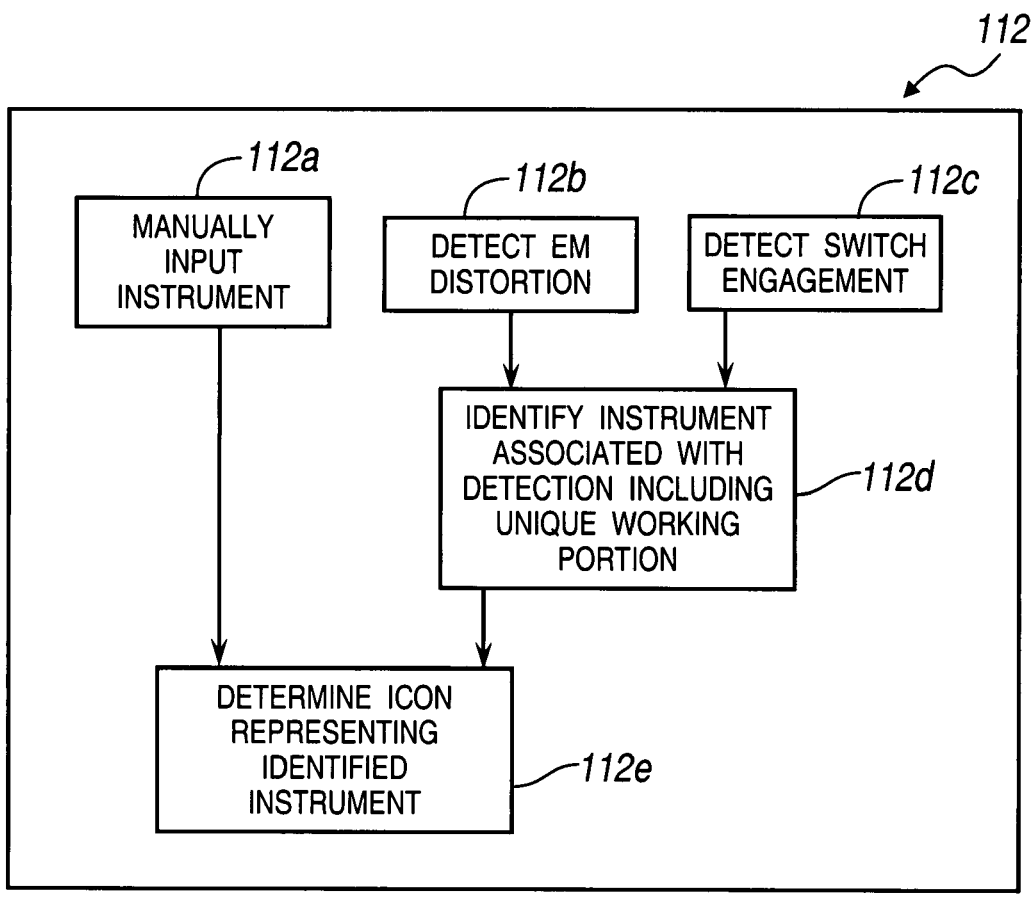
FIG. 2B is a detailed view of an automatic identification.

With reference to FIG. 2B, the identification of the selected instruments in block 112 can occur according to the various methods briefly illustrated in FIG. 2A. The identification processes, illustrated in block 112, however, are illustrated in further detail in FIG. 2B. As discussed above, the various types of identification can include manually inputting the instrument in block 112a, detecting EM distortion in block 112b, and detecting a switch engagement in block 112c.

If the instrument is identified via manually inputting the instrument in block 112a, then determination of an icon representing the identified instrument can be reached substantially immediately in block 112e. Determining the icon representing the identified instrument can occur according to any appropriate embodiment, such as accessing a lookup table of icons and selecting the appropriate icon, drawing an icon based upon the unique working portion or feature of the instrument, or any other appropriate method.

Also the instrument can be identified by detecting the EM distortion in block 112b, with the appropriate system. As discussed above, the tracking system 50 can be the system that is used to detect the EM distortion. It will also be understood that any other appropriate system can be provided to detect or determine the EM distortion in block 112b. Once the EM distortion is detected in block 112b an identification of the instrument, and its associated unique working portion, can be determined block 112d. As discussed further herein, the various unique working portions can include an awl portion, a tap portion, a probe portion, a driver portion, a cannula, a length dimension, a cross-section dimension, or any other unique working portion or unique feature of an instrument.

The identification of the instrument can include various steps, such as accessing a lookup table, accessing a table of measurements, or any other appropriate step. Nevertheless, once the instrument is identified in block 112d, based upon the detection, determining an icon representing the identified instrument can occur in block 112e. The determination of the icon can occur according to any appropriate method, as discussed above. Methods, according to various embodiments, include accessing a database of icons or drawing an icon.

If the instrument 24 or tip portion is detected with a switch, then detection of the switch engagement can occur in block 112c. Following the detection of the appropriate switch engagement, the identification of the instrument and the determination of the icon, in blocks 112d and 112e respectively, can follow as discussed above. Detection of the switch engagement, in block 112c, can be any appropriate type. For example, a physical feature of the tip can engage a physical switch or mechanical switch on the handle. Nevertheless, a switch engagement can also include an electronic switch engagement, an optical switch engagement, or any appropriate switch engagement. According to any appropriate method, however, the substantially automatic detection of the instrument can occur and be used by the navigation system 10 to navigate an instrument relative to the patient 28.

Figure 3:
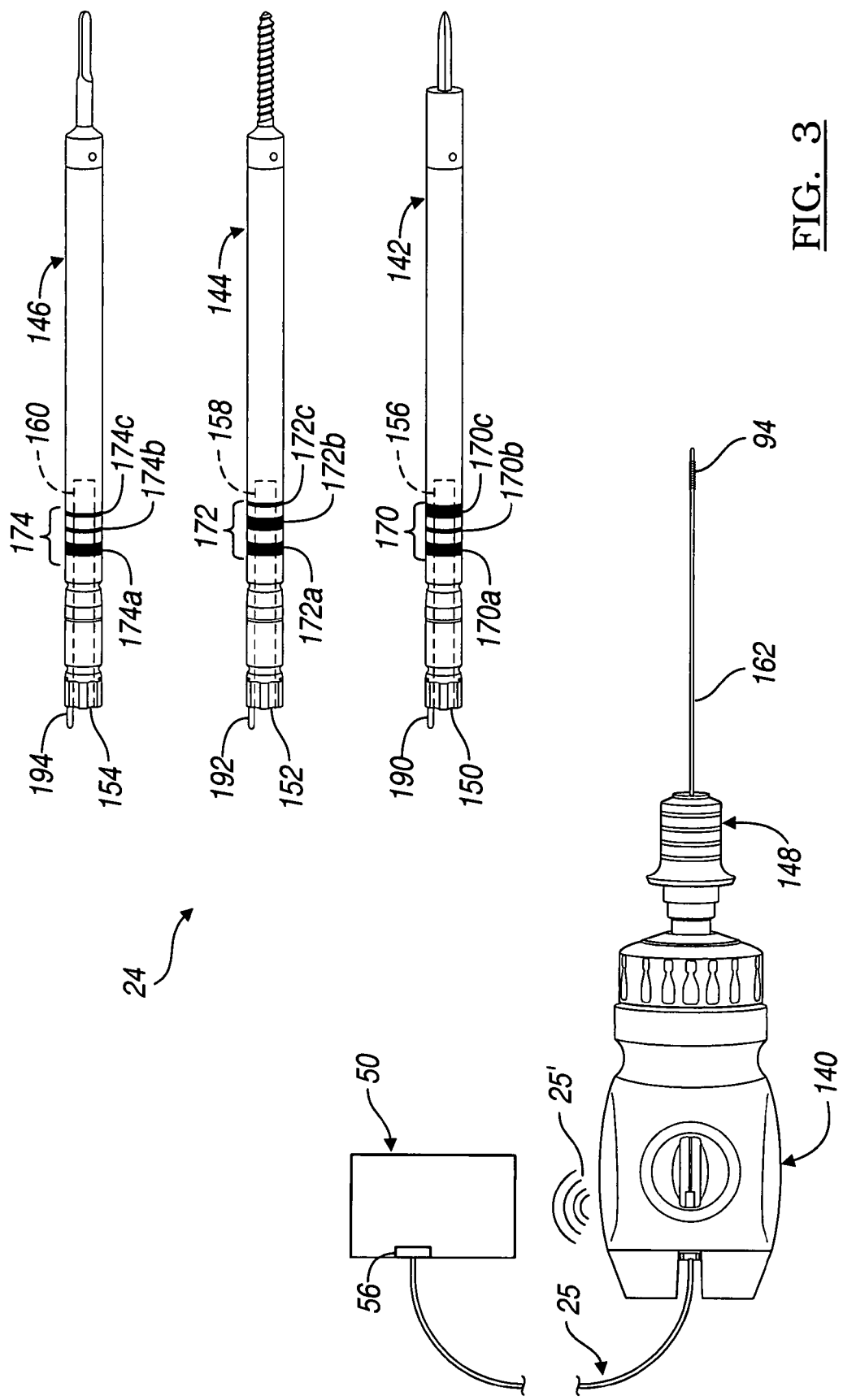
FIG. 3 is a top view of an instrument handle and tip with identification portions according to various embodiments.

With reference to FIG. 3, according to various embodiments, the instrument 24 can, exemplarily, include a multi-tip instrument. The instrument 24 can include a handle portion 140 and various tip portions, including an awl 142, a tap 144, and a probe 146. The various tips 142-146 can interconnect with the handle 140 through an interconnection portion 148. The handle interconnection portion 148 can interconnect with a connection portion of the various tips 142-146, such as an awl connection portion 150, a tap connection portion 152, and a probe connection portion 154. The connection portions can include any connection portions, such as a quick connect, a twist lock, a snap-fit, or the like.

Each of the tip portions 142-146 can also include a respective stylet canal or channel 156, 158, 160. The stylet channels 156-160 can receive a stylet 162. The stylet 162 can include various portions, such as a tracking device 94. The stylet can be any appropriate stylet, such as the stylet disclosed in pending U.S. patent application Ser. No. 11/241,837 filed on Sep. 30, 2005 entitled, "Method and Apparatus for Surgical Navigation", incorporated herein by reference.

The stylet 162 can act as the tracking device and specifically include the tracking device coil 94. The tracking device 94 can include a plurality of coils, such as three or more selectively configured coils that can interact with the tracking system 50, such as sensing a position of the stylet 162 within the field produced by the localizers 52, 52a. Nevertheless, as discussed above, the tracking device 94 can also transmit a field that is received by the localizers 52, 52a. Nevertheless, the instrument 24 can communicate within the tracking system 50 via the communication line 25. It will be understood, however, that a substantially wireless system can also be provided so that a wireless signal 25' can also alternatively be provided as the communication line with the tracking system 50.

As discussed above, the tracking system 50 can include a substantially electromagnetic system. Also as discussed above, the electromagnetic tracking system can generally determine a position of the tracking device 94 within the field produced by the localization devices 52, 52a. The field, however, can be distorted with various portions, such as ferromagnetic or conductive materials. As one skilled in the art will understand, conductive materials can interfere with the uniformity of magnitude of the field and distort the signal produced by the instrument 24 or received by the tracking device 94 from the localizers 52, 52a. The various tips 142-146 can include identification distortion members or sections. For example, the awl can include a first identification section 170, the tap 144 can include a second identification section 172, and the probe 146 can include a third identification section 174.

The various identification sections 170-174 can include specific portions, such as identification bands. The identification bands can include substantially annular portions that completely surround the channels 156-160. Alternatively, the identification bands can be provided to only partially surround or be positioned adjacent the channels 156-160.

The identification bands can be provided or formed of any appropriate material. For example, the identification bands can be formed of conductive metals or polymers. Also, the identification bands can be ferrous materials. The identification bands can shield either a reception or transmission of a signal from the tracking member 94. The shielding can occur by providing a ground to the identification bands so that they interfere with the signal transmitted or received from the tracking member 94.

The shielding can produce a loss in signal strength for a period of time. Lowering the signal strength or series of signal strength decreases can be used as the identification signal. The number, length, and variation of signal strength decreases can be used to identify the instrument. The decreases can occur as the tracking member 94 moves passed the identification bands.

For example, the identification section of the awl 170 can include a first large band 170a, a second small band 170b, and a third large band 170c. The identification section of the tap 172 can include a first large band 172a, a second large band 172b, and a third small band 172c. Also, the identification section of the probe 174 can include a first large band 174a, a second small band 174b, and a third small band 174c. The various identification sections 170, 172, and 174, therefore, can each be substantially distinct and different from the other.

Because the stylet channels 150-154 are formed through a plane defined by each of the bands of each of the identification sections 170-174, the tracking device 164, defined by the stylet 162, can determine the affect of the identification sections 170-174 on the field sensed or received by the tracking device 94, as briefly described above. For example, as the tracking device 94 passes through the stylet channel 150 in the awl 142, the field can be disturbed by the identification section 170 first by a long distortion, then by a short distortion, then by a long distortion. The various distortions can be produced by the bands 170a-170c of the awl identification section 170.

The distortion can then be transmitted via the communication system 25 to the work station 42 for appropriate identification of the awl 142. Therefore, the selection of the instrument can be made to be the awl 142, such as in block 108, and identified substantially automatically in block 110 with EM distortion, as described in block 112. Any other appropriate instrument can also be identified.

Also, as discussed above, the EM distortion can be produced by the identification section of the awl 170 in any appropriate manner. For example, the bands 170a-170c can be formed integrally with the awl 142, formed on an interior diameter, such as near the channel 156, or at any appropriate position to interfere with the field sensed or transmitted by the tracking device 164. As the tracking system 50 detects the distortions they can be used to identify the instrument 24. The distortions can be determined in the CAC 54, work station 42, or any appropriate portion. Identification can include accessing a look-up table of "distortion codes" to identify the instrument tip.

It will be understood, however, that any appropriate identification member reader can be provided. The identification member reader can be integrally provided, as a single system, with the tracking system 50 or as a separate system. The identification member reader can be a separate system or part of any other appropriate system to receive the signal produced by the identification sections. As discussed herein, the identification sections can be either EM distortion portions, switches, or any appropriate portion. Thus, the identification member reader can be provided to receive a signal from any of the appropriate identification portions.

The identification sections 170-174 can be formed of any appropriate material, such as a ferrous material, a conductive polymer, or the like. Thus, the EM distortion produced by the identification sections 170-174 can be used to identify the first selected instrument in block 110. The appropriate or identified instrument can then be displayed as icon 24' on the display 22 as in block 114. A selected portion of the procedure can then be navigated as in block 116.

As discussed above, the tracking system 50 can be provided to work with the identification sections. For example, as the tracking device 94 moves passed the identification sections, a distortion or decrease in the signal received by the tracking device 94 or the localizer 56 (depending upon whether the tracking device 94 receives or transmits) can occur. This decrease in signal, produced by the identification sections, can be transferred to the workstation 42 and used to identify the instrument that is attached to the handle 140. The processor system 40 can be used to both identify the instrument and tracking the tracking device 94.

Also, as illustrated in the identification method 100, any other portion can also be interconnected with the handle 140 to be identified with the tracking device 94. Therefore, the various tips 142-146 can be used in succession, repeatedly used, or any appropriate manner with the handle 140 to perform a procedure.

The various tips 142-146 can also include an engagement or keyed portion 190, 192, 194 respectively on the awl 142, the tap 144, and the probe 146. The engagement or keyed portions 190-194 can engage a keyed portion in the handle 140, such as the connection portion 148, to insure that the tip portion 142-146 is oriented in an appropriate selected manner with the handle 140 and to insure that the stylet 162 is appropriately positioned with the tip 142-146. This can help insure that the tracking device 94 of the stylet 162 appropriately reads the identification section 170-174 of the tips 142-146. It will also be understood that any appropriate number of tips can be provided. For example, the probe 146 can be provided in a plurality of lengths, configurations, sizes or the like. Also, the tap 144 can also be provided in various sizes for different users. Also, completely different instruments can be provided to interconnect with the handle 140 and can also include selected identification sections to identify the selected tip. Alternatively or in addition, separate instruments can include identification portions to be read with the tracking device 94.

The identification can also include a chart or table within the memory 46 of the work station 42. Therefore, as the identification section 170-174 affects the field sensed or sent by the tracking device 94, the work station 42 can use the received information to compare to the table in the memory 46 to identify the tip or instrument portion. This information can then also be connected or used to identify appropriate sizes, configurations, and the like to insure an appropriate identification or display of the icon 24' on the display 22.

Figure 4:
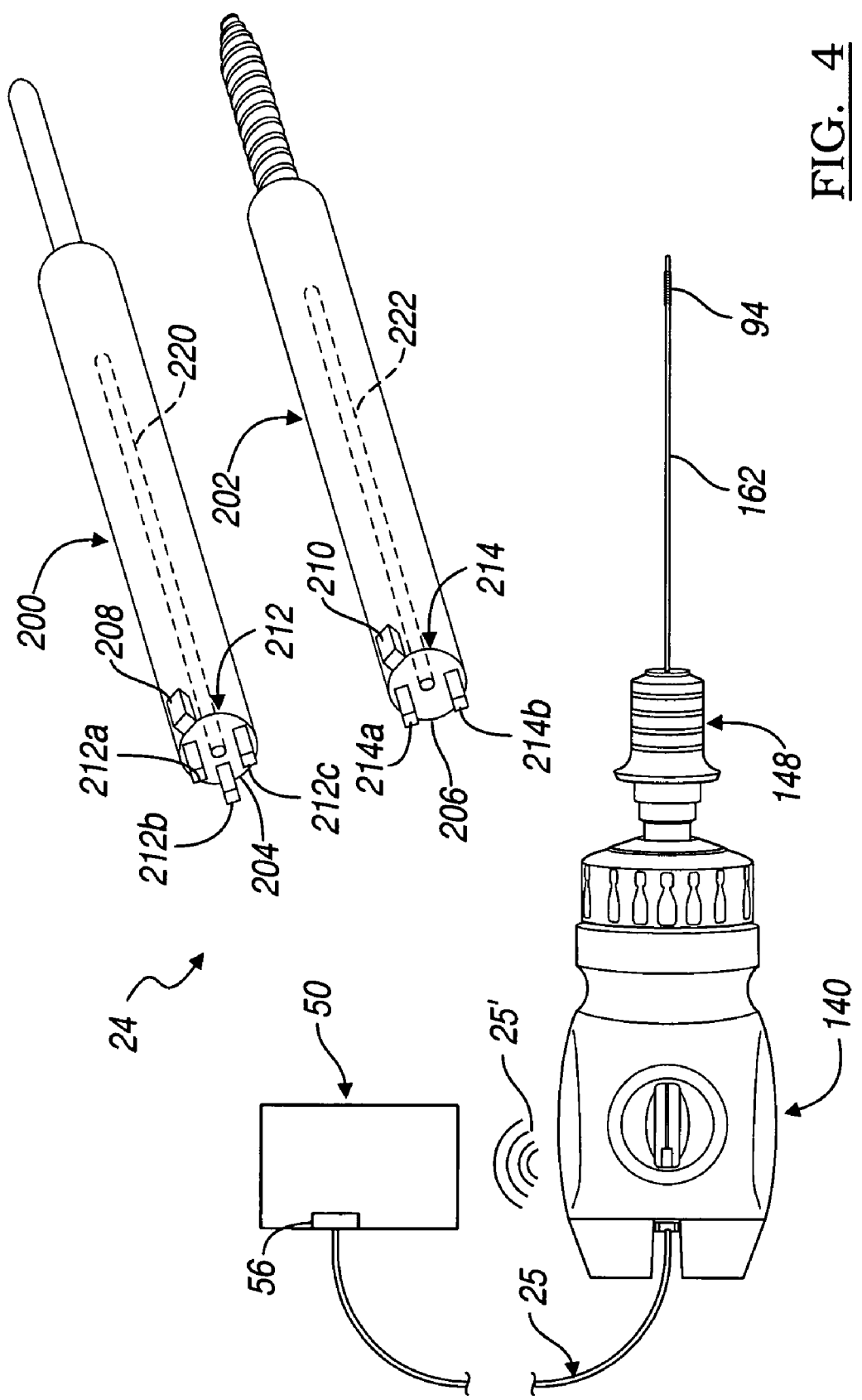
FIG. 4 is a top view of an instrument handle and several tips with identification portions according to various embodiments.

With reference to FIG. 4, the instrument 24 can be provided according to various embodiments. Again, the handle 140 can be provided with a tip connection portion 148. The tip connection portion can interconnect with various tips, such as a probe tip 200 or a tap tip 202. It will be understood that any appropriate number of tips can be provided and the two tips 200, 202 are merely exemplary. Further, each of the tips 200, 202 can include a connection section 204 on the probe 200 and 206 on the tap 202. The connection sections 204, 206 can include a key portion 208, 210 respectively. The key portions 208, 210 can insure that the tips 200, 202 engage the tip engagement section 148 of the handle 140 in a substantially congruent manner. This allows the tips 200, 202 to engage the handle 140 in substantially only a single orientation. This can allow for each of the tips 200, 202 to be identified by the tracking system 50 or the navigation system 20. Positioned near the engagement ends 204, 206 can be an identification section 212, 214 respectively.

The identification sections 212, 214 can include projections or switch engagement members. For example, the identification section 212 can include a first switch engagement member 212a, a second switch engagement member 212b, and a third switch engagement section 212c. The switch engagement sections 212a212c can be projections that can engage one of a plurality of switches or connection points on the handle 140. As the probe tip 200 engages the tip engagement section 148, the key portion of the probe 208 can insure the proper orientation of the probe 200 relative to the tip engagement section 148. The engagement member's 212a212c can then engage connections, switches, or the like to allow for a determination or a transmittal of an appropriate identification signal. The connections or switches can make a signal that is used by the navigation system 20 to identify the tip 200 in a manner similar to that discussed above.

The tap 202 including the identification section 214 can include two identification members 214a and 214b. The identification members 214a, 214b can be in a different position, orientation, or the like relative to the key portion 210 and the engagement member's 212a212c of the identification section 212 of the probe 212. Therefore, the projections 214a, 214b can engage different switches, connections, or the like when engaged on the tip engagement section 148. Again, the keyed portion of the tap 210 can insure an appropriate orientation of the tap 202 relative to the tip engagement section 148.

It will be understood that any appropriate number of engagement sections can be provided in an appropriate identification section for providing an appropriate engagement with the engagement member 148. Therefore, the identification of the first selected instrument in block 110 can use the switch engagement illustrated in block 112. This can allow for the identification of the first selected instruments and the display of the first selected instrument in block 114 It will be further understood that the memory 46 of the work station 42 can include a look-up table that includes the appropriate information for determining the tip that engage the engagement section 148 of the handle 140. This information can be transferred along the transmission line 25 to the interface 56.

Each of the tips 200, 202 can also include a stylet bore. The probe 200 can include a first bore 220 and the tip 202 can include a second bore 222. The bores 220, 222 can receive the stylet 162 and the tracking device 94 for tracking in the tracking system 50. It will be understood that the tracking device 94 can also be integrated into the tip 200, 202 in any appropriate manner.

Therefore, one skilled in the art will understand that the identification of the instrument, or a portion interconnected with the instrument 24, can be substantially automatic according to various embodiments. The identification of the instrument or selected portion of the instrument can allow for an automatic identification of the instrument and display on the display 22 or navigation by the navigation system 20, with or without a display. This can alleviate or reduce the interaction required by a user, such as the surgeon 21, to perform a selected procedure.

The automatic identification system can also be used as an error check or determination system. For example, a preoperative plan can be created and loaded into the memory 46 and accessed by the work station 42. The preoperative plan can include identification of areas to be intervened in, instruments to be used, timing of instruments to be used, instruments to be positioned in various portions of the anatomy of the patient 28, or the like. Therefore, the automatic identification of the instrument or portion of the instrument 24 can be used and compared to the preoperative plan to assist in insuring an appropriate plan is carried out. Therefore, the automatic identification of the instrument can assist in determining that an appropriate instrument is being used, a position of an appropriate instrument, or the like.

Further, the various switches can insure that the appropriate instrument is fully seated within the handle 140. The use of the multiple tips relative to the handle 140 can be assisted by the use of the switches to insure that they are positioned relative to the handle 140 in a selected manner. This can help insure that the tip is positioned relative to the handle in the predetermined position for appropriate navigation or display of the instrument on the display 22 or for navigation of the instrument 24.

Further, the identification substantially automatically if an instrument, according to various embodiments, can assist in a procedure. The identification of the instrument substantially automatically can allow for minor variations in various instruments or instrument tips that are not easily distinguishable by a user. Therefore, the automatic identification of the instrument can alleviate or substantially eliminate the possibility of mistaken identification of an instrument portion. Further, the user, such as the surgeon 21, can quickly switch instruments or instrument portions without manually determining the instrument being applied for navigation.

The teachings herein are merely exemplary in nature and, thus, variations that do not depart from the gist of the teachings are intended to be within the scope of the teachings. Such variations are not to be regarded as a departure from the spirit and scope of the teachings.

What is claimed is:

1. A navigation system to navigate a procedure on an anatomy, comprising:
    an instrument having a first portion and a second portion configured to be moved relative to the anatomy, wherein at least one of the first portion or the second portion comprises a passage;
    an identification member including field distortion members coupled to one of the first portion or the second portion;
    a tracking device passed through the passage comprised in the first portion or the second portion of the instrument and configured to be tracked, the tracking device responsive to the field distortion members to obtain identification information regarding an identification of the instrument; and
    a processor operable to identify the instrument based at least in part on the identification information obtained from the tracking device.

2. The navigation system of claim 1, wherein the first portion is a first member and the second portion is a second member connected with the first member.

3. The navigation system of claim 2, wherein the second portion is interconnected with the first portion at a selected time and includes the identification member.

4. The navigation system of claim 3, wherein the identification member is operable to distort a field as the second portion is interconnected with the first portion.

5. The navigation system of claim 1, further comprising:
an electromagnetic localization system;
wherein the electromagnetic localization system is operable to at least one of produce an electromagnetic field, receive an electromagnetic field, or combinations thereof.

6. The navigation system of claim 5, wherein the tracking device senses distortions in the electromagnetic field produced by the electromagnetic localization system based upon the identification member, including the identification member shielding the tracking device from the electromagnetic field, wherein the shielding can occur by providing a ground to the identification member so that the identification member interferes with a signal transmitted or received from the tracking device.

7. The navigation system of claim 6, further comprising:
a memory system;
wherein the processor receives the identification information including the field distortion information from the tracking device and accesses the memory system to determine a particular identification of the instrument.

8. The navigation system of claim 7, further comprising:
a display device;
wherein the display device is operable to display an icon representing the specific instrument based upon the identification made by the processor.

9. The navigation system of claim 1, wherein the field distortion members include a plurality of conductive or ferromagnetic annular rings disposed about the passage of the instrument and axially spaced along the instrument.

10. The navigation system of claim 1, further comprising:
a memory system, including a database of the information;
wherein the processor is operable to determine the identity of the instrument based upon the identification information in the memory system by at least comparing the identification information obtained by the tracking device from the identification member to the database.

11. The navigation system of claim 1, further comprising:
a tracking system to track the tracking device, wherein the processor is integral with the tracking system.

12. The navigation system of claim 1 further comprising:
an imaging system operable to obtain image data of the anatomy.

13. The navigation system of claim 12, further comprising:
a display operable to display an icon representing the identified instrument based upon a determination of the processor.

14. The navigation system of claim 1, wherein the instrument includes at least one of an awl, a probe, a tap, a driver, a stint, or combinations thereof.

15. A navigation system to navigate a procedure on an anatomy, comprising:
an instrument operable to be moved relative to the anatomy, the instrument defining a channel in and through at least a portion of a length of the instrument;
at least one conductive identification band positioned around the channel in the instrument;
an electromagnetic tracking device moveable within the channel of the instrument and responsive to the at least one conductive identification band to obtain identification information regarding an identification of the instrument and further configured to move with the instrument to be tracked in physical space;
a tracking system that generates an electromagnetic field for tracking the electromagnetic tracking device as the electromagnetic tracking device and the associated instrument move in physical space; and
a processor that identifies the instrument based at least in part on the identification information obtained by the tracking device from the identification band.

16. The navigation system of claim 15, wherein the at least one conductive identification band causes at least one decrease in a signal received by the tracking device at least by shielding the electromagnetic tracking device by providing a ground to the at least one conductive identification band so that the at least one conductive identification band interferes with the signal transmitted or received from the electromagnetic tracking device, which is used to identify the instrument.

17. The navigation system of claim 15, wherein the instrument comprises three conductive identification bands, each causing a distortion in a signal received by the tracking device as the tracking device moves through the channel of the instrument, which is used to identify the instrument.

18. A navigation system to navigate a procedure on an anatomy, comprising:
an instrument to move relative to the anatomy, the instrument having a handle member and a plurality of tip members, each of the plurality of tip members comprising a channel in and through at least a portion of a length of respective tip members;
at least one conductive identification band positioned around each channel in each of the plurality of tip members;
a tracking system having,
a localizer that generates an electromagnetic field; an electromagnetic tracking device moveable within the channel of the tip member and past the at least one conductive identification band to obtain identification information regarding an identification of the instrument at least by shielding the electromagnetic tracking device from the generated electromagnetic field and further configured to move with the instrument to be tracked in physical space;
a tracking processor for tracking the electromagnetic tracking device as the electromagnetic tracking device and the associated instrument move in physical space; and
processor that identifies which of the plurality of tip members is presently positioned over the electromagnetic tracking device based at least in part on the identification information obtained by the tracking device from the identification band.

19. The navigation system of claim 18, wherein the at least one conductive identification band shields a signal from or a signal to the electromagnetic tracking device for a selected length as the electromagnetic tracking device is moved into the channel.

20. The navigation system of claim 18, wherein the at least one conductive identification band includes at least two conductive identification bands wherein each of the two conductive identification bands shields the electromagnetic tracking device separately.

21. The navigation system of claim 18, wherein the processor receives the signal from the electromagnetic tracking device.

22. The navigation system of claim 21, wherein the processor and the tracking processor are the same processor.

* * * * *